(12) United States Patent
Dorvee et al.

(10) Patent No.: US 7,684,043 B2
(45) Date of Patent: Mar. 23, 2010

(54) SYSTEM AND METHOD FOR REMOTE, FREE-SPACE OPTICAL DETECTION OF POTENTIAL THREAT AGENT

(75) Inventors: Jason R. Dorvee, Ithaca, NY (US);
Jamie R. Link, Arlington, VA (US);
Michael J. Sailor, La Jolla, CA (US);
Harold E. Hager, Bellevue, WA (US);
William D. Sherman, Kent, WA (US)

(73) Assignees: University of California; The Boeing Company, Chicago, IL (US)

( * ) Notice: Subject to any disclaimer, the term of this patent is extended or adjusted under 35 U.S.C. 154(b) by 301 days.

(21) Appl. No.: 11/680,309

(22) Filed: Feb. 28, 2007

(65) Prior Publication Data

US 2008/0204752 A1 Aug. 28, 2008

(51) Int. Cl.
*G01N 21/49* (2006.01)
(52) U.S. Cl. .................................. 356/437; 356/446
(58) Field of Classification Search .......... 356/335–343, 356/73, 301, 432–440, 445–448
See application file for complete search history.

(56) References Cited

U.S. PATENT DOCUMENTS

| | | | |
|---|---|---|---|
| 5,257,085 A | 10/1993 | Ulich et al. | |
| 5,898,373 A | 4/1999 | Murad et al. | |
| 6,066,295 A | 5/2000 | Bernstein | |
| 6,867,052 B2 * | 3/2005 | Lander et al. | 436/518 |
| 7,319,039 B2 * | 1/2008 | Sullivan | 436/172 |
| 7,359,056 B2 | 4/2008 | Koshinz | |
| 2006/0262299 A1 | 11/2006 | Hager | |
| 2007/0035730 A1 * | 2/2007 | Koshinz | 356/338 |

OTHER PUBLICATIONS

Schmedake, Thomas A.; Cunin, Fréderique; Link, Jamie R.; and Sailor, Michael J. "Standoff Detection of Chemicals Using Porous Silicon 'Smart Dust' Particles", Advanced Materials, vol. 14, No. 18, Sep. 16, 2002, pp. 1270-1272.
Sailor, Michael J. and Link, Jamie R. "'Smart Dust': Nanostructured Devices in a Grain of Sand", The Royal Society of Chemistry 2005, pp. 1375-1383.

(Continued)

*Primary Examiner*—Hoa Q Pham
(74) *Attorney, Agent, or Firm*—Harness, Dickey & Pierce, P.L.C.

(57) ABSTRACT

A system and method for free space, optical remote sensing of a potential threat agent using spectrally responsive sensor material. In one example the sensor material is formed by particles, which in one particular form are porous photonic crystals. The particles are dispersed into an area being monitored for the presence of the potential threat agent. A pair of lasers is used to generate optical light beams that are directed at the sensor particles after the particles have been dispersed. The light reflected by the sensor particles is then analyzed. The presence of the potential threat agent causes a shift in the spectral peak of light reflected from the sensor particles that can be sensed using photo detectors and a processing subsystem. The system can be tuned to remotely detect for specific chemical, biological or environmental agents that may be present within a given area.

20 Claims, 4 Drawing Sheets

OTHER PUBLICATIONS

Cunin, Frédérique; Schmedake, Thomas A.; Link, Jamie R.; Li Yang Yang; Koh, Jennifer; Bhatia Sangeeta N.; and Sailor, Michael J. "Biomolecular Screening with Encoded Porous-Silicon Photonic Crystals", Nature Publishing Group, Nature Materials, 3 pages. Published online, Sep. 2, 2002; doi:10.1038/nmat702, 3.

Dorvee, Jason R.; Derfus, Austin M.; Bhatia, Sangeeta N.; and Sailor, Michael J. "Manipulation of Liquid Droplets Using Amphiphilic, Magnetic One-Dimensional Photonic Crystal Chaperones", Nature Publishing Group, Nature Materials, vol. 3, Dec. 2004, pp. 896-899. Published online: Nov. 7, 2004; doi:10.1038/nmater1253.

Link, Jamie R. and Sailor, Michael J. "Smart dust: Self-Assembling, Self-Orienting Photonic Crystals of Porous Si", PNAS, vol. 100, No. 19, Sep. 16, 2003, pp. 10607-10610. www.pnas.org/cgi/doi/10.1073/pnas.1233824100.

Database Compendex [online] Engineering Information, Inc., New York, NY, US; Jun. 8, 2005, Dorvee, J. et al. "A low-power sensor for volatile organic compounds based on porous silicon photonic crystals", XP002502514, database accession No. E2005409398417, the whole document, and Physica Status Solidi (A) Applications and Materials, Jun. 2005, Wiley-VCH Verlag, DE, vol. 202, No. 8, Jun. 2005, pp. 1619-1623.

* cited by examiner

SYSTEM AND METHOD FOR REMOTE, FREE-SPACE OPTICAL DETECTION OF POTENTIAL THREAT AGENT

STATEMENT OF GOVERNMENT RIGHTS

This invention was made with Government support under W911SR-04-C-0094 awarded by DARPA. The government has certain rights in this invention.

FIELD

The present system and method relates to systems for detecting material that may pose a chemical, biological or environmental threat to human health or to property. More particularly the present system and method relates to an optical system for remotely sensing the presence of chemical, biological or environmental threat material or other potentially deleterious agents.

BACKGROUND

The statements in this section merely provide background information related to the present disclosure and may not constitute prior art.

The detection of industrial chemical toxicants, chemical warfare agents, environmental toxins, and even explosives, represents an ongoing challenge. Often, systems that have been constructed for such a purpose have proven to be expensive, relatively complex, or to be otherwise limited in effectiveness. In addition, when detecting the presence of hazardous substances within a given area, it would be highly desirable to avoid having an individual enter the area in question even if the individual is wearing suitable protective clothing. The ability to remotely detect the presence of chemical, biological, explosive and environmental agents within a given area, from a remote location, adds an additional degree of assurance to the well being of those individuals operating such a detection system. Such a system could also have wide ranging applicability in the medical and food and/or drug industries.

SUMMARY

The present disclosure is related to a system and method for free space, optical remote sensing for a potential threat agent. The threat agent may comprise a chemical, biological or environmental material that poses a threat to human health. In one embodiment, the system includes a first laser that is tuned to emit optical radiation at a first wavelength. A second laser is tuned to emit optical radiation at a second wavelength that is different from the first wavelength. A sensor agent is placed in an area in which the detection of a potential threat agent may or may not be present. The sensor agent is constructed having a characteristic such that a wavelength of an optical signal reflected by the sensor agent has a spectral peak that closely approximates the first wavelength, in the absence of the potential threat agent. However, when the potential threat agent is present around the sensor agent, light reflected from the sensor agent will have its spectral peak shifted by at least a small degree. In one embodiment, the shifting of the spectral peak moves toward the value of the second wavelength.

A subsystem is provided that receives and analyzes optical radiation generated by the first and second lasers that is reflected from the sensor agent. The subsystem determines if a shift has occurred in the spectral peak of the optical signal reflected from the sensor agent when the sensor agent is disposed in the predetermined area of interest. A shift of a predetermined magnitude of the spectral peak of the optical signal reflected from the sensor agent indicates the presence of the potential threat agent.

In one embodiment, the subsystem includes first and second detectors, with the first detector receiving the first wavelength optical signal that is reflected from the sensor agent, and the second detector receiving the second wavelength optical signal that is reflected from the sensor agent. The intensity of the two reflected optical signals is measured by the first and second detectors. A processing subsystem receives an output from each detector and compares the intensities of the two reflected optical signals. From the comparison, a determination is made as to whether the potential threat agent is present.

In another embodiment a single time-resolved detector is used to receive both of the first and second reflected optical signals from the sensor agent. In this embodiment the optical signals generated by the first and second lasers are modulated at different frequencies and the time-resolved detector is synchronized to periodically, alternately sample both of the reflected optical signals from the sensor agent.

In one embodiment, the sensor agent is comprised of porous photonic crystals. The crystals are manufactured such that a spectral peak of an optical signal reflected from the crystals, when the crystals are not in the presence of the potential threat agent, has a frequency approximately equal to the first wavelength of the first optical signal. In another embodiment, the porous photonic crystals are made up of porous silicon photonic crystals.

In one implementation a method is disclosed for performing free space, optical remote sensing for a potential threat agent. The method may include the operations of forming a sensor from particles having specific desired spectral characteristics so that optical radiation reflected from the particles has a spectral peak at a first predetermined wavelength when the potential threat agent is not present in a vicinity of the particles, but where the spectral peak shifts when the sensor particles are located within a potential threat agent. First and second optical beams are used that have different wavelengths to irradiate the sensor particles. The first and second optical beams are analyzed after they have been reflected from the sensor particles to determine if the detected intensity of one of the reflected optical beams has decreased, while the intensity of the other reflected optical beam has increased. When such a condition occurs, this indicates that the spectral peak of one of the reflected optical beams has shifted. The shifting indicates the likely or certain presence of the potential threat agent.

Further areas of applicability will become apparent from the description provided herein. It should be understood that the description and specific examples are intended for purposes of illustration only and are not intended to limit the scope of the present disclosure.

BRIEF DESCRIPTION OF THE DRAWINGS

The drawings described herein are for illustration purposes only and are not intended to limit the scope of the present disclosure in any way.

DETAILED DESCRIPTION

The following description is merely exemplary in nature and is not intended to limit the present disclosure, application, or uses.

Figure 1:
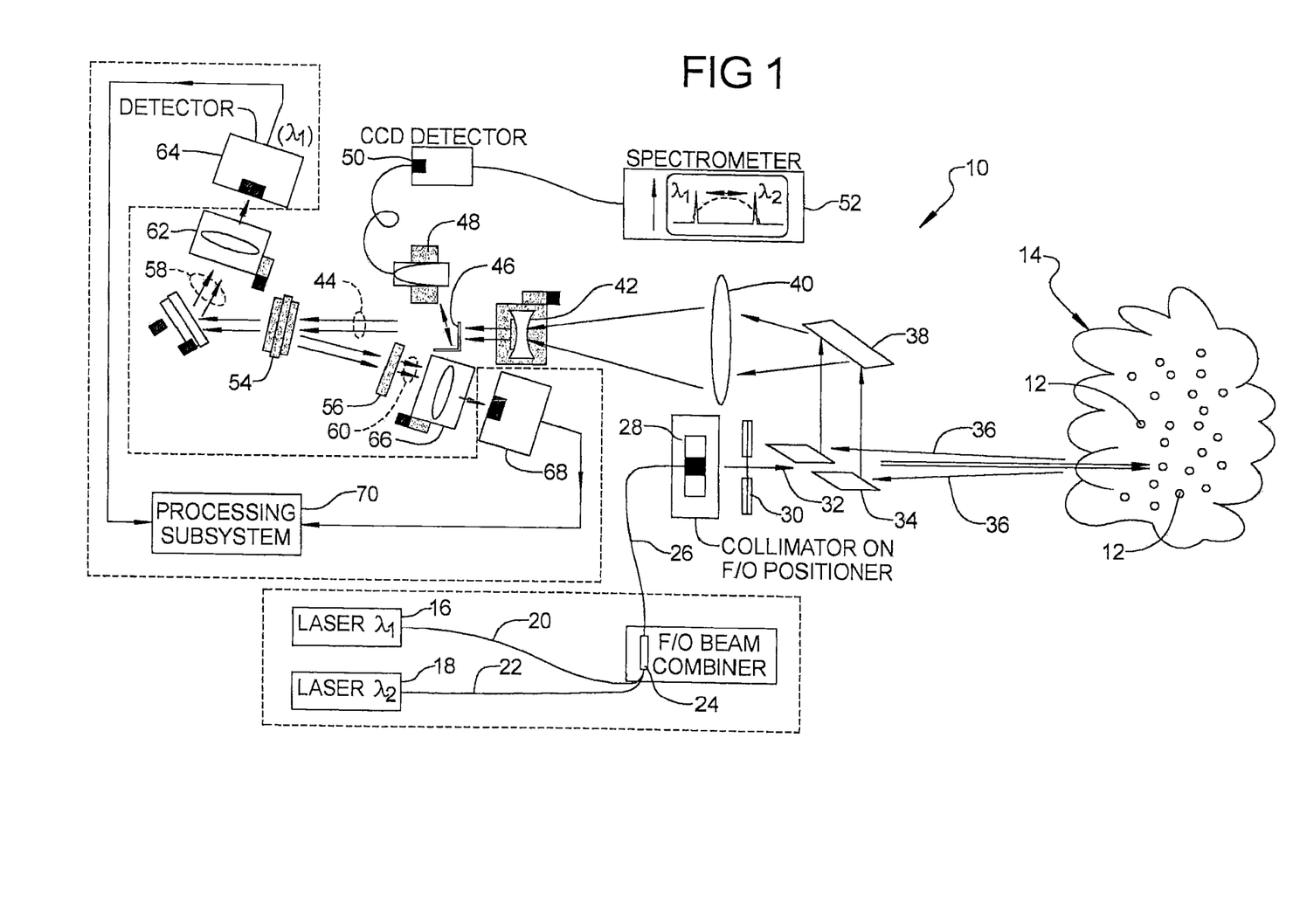
FIG. 1 is a block diagram of a system in accordance with one embodiment of the present disclosure

Referring to FIG. 1, a system 10 is illustrated for optical, free space remote sensing of a potential threat agent. In this example, the potential threat agent represents a cloud or plume 14 within which a sensor agent, represented by particles 12, has been dispersed. As will be described further in the following paragraphs, the sensor particles 12 are constructed with specific, desired spectral characteristics so that light reflected by each of the sensor particles 12 has a spectral peak at a predetermined wavelength. The system 10, in the exemplary embodiment of FIG. 1, includes a first laser 16 and a second laser 18. The first laser 16 generates a coherent first optical beam of light having a first wavelength, for example, 640 nm. The second laser 18 generates a second optical beam of coherent light having a different wavelength from that of the optical beam generated by the first laser 16. The wavelength of the light beam generated by the second laser 18, in this example, may be 660 nm. It will be appreciated that these exemplary wavelengths may be altered as needed for specific applications, and that the wavelengths of the optical beams generated by the lasers 16 and 18 will depend at least in part on the spectral characteristics that the sensor particles 12 are constructed to have. It will be appreciated that in lieu of a pair of lasers 16 and 18, that a single laser with a tunable emission energy could be incorporated. The single laser could have its laser emission wavelength scanned and detected over a range of energies that encompass the energies of the spectral peaks of interest.

The first and second optical beams from the first and second lasers 16 and 18, respectively, are transmitted through fiber optic cables 20 and 22, respectively, to a fiber beam combiner 24. The two optical beams are combined in the beam combiner 24 and pass through a third fiber optic cable 26 to a collimator 28. The collimator 28 combines the two light beams and passes the beams through an iris 30 that further focuses the two beams into a single beam. The single optical beam is represented by arrow 32. The single optical beam 32 passes through the center hole of a collection mirror 34 and irradiates at least a subquantity of the sensor particles 12 dispersed in the cloud 14. In this example, the sensor particles 12 have been constructed with a spectral characteristic that causes light reflected from the sensor particles to have a spectral peak of approximately 640 nm when the particles are disposed in free air (in the absence of the potential threat agent). The 640 nm wavelength of reflected light from the sensor particles 12 will thus approximately match the wavelength of the first optical beam generated by first laser 16.

It will be appreciated that the particles 12 are also constructed such that the presence of a specific chemical, biological or environmental agent around the particles will cause a known shift in the spectral peak of light reflected by the particles 12. In this example, the cloud or plume 14 may represent isopropyl alcohol vapor that will cause a shift in the spectral peak of light reflected by the particles 12 towards the 660 nm wavelength of the light generated by the second laser 18. It will also be appreciated that through empirical testing with different threat agents, that a known degree of shifting of reflected light can be expected. Thus, the lasers 16 and 18 can be selected or tuned to produce optical beams having particular wavelengths that are intended to detect the presence of specific threat agents.

With further reference to FIG. 1, the sensor particles 12 may be delivered into the cloud or plume 14 by any suitable method, such as by an unmanned air vehicle (UAV) or a ground vehicle, or possibly even a marine vessel. In an alternate configuration employing this same optical interrogation approach, the sensor particles 12 could be substituted for a sensor material that is not in particle form. For example, a sensor material could be deployed in a fixed (non-particulate) configuration, e.g., as an appliqué (e.g., wafer) positioned adjacent a structure such as a building, dwelling or antenna tower, on a stationary vehicle, or even carried on the clothing of an individual. In any application, the only requirement is that the sensor material (i.e., either sensor particles 12 or some other form of sensor material) be located/positioned in a manner that enables them to be optically interrogated. In the example shown in FIG. 1, the sensor particles 12 could also be delivered into the cloud or plume 14 via a projectile that releases the particles 12 at a desired elevation or upon contacting a ground surface over which the cloud or plume 14 is present.

Referring further to FIG. 1, an optional arrangement of components to achieve a higher degree of spectral resolution involves directing optical beams 36 reflected from the sensor particles 12 into a collection mirror 34. The reflected optical beams 36 are then further reflected by the collection mirror 34 to another mirror 38. Mirror 38 reflects the reflected optical beams 36 through a focusing lens 40 that further focuses the reflected optical beams 36 into a focusing lens 42. The focusing lens 42 focuses the two reflected optical beams 36 essentially into one focused beam that is made up of the plurality of reflected optical beams 36. The single reflected beam is denoted by arrows 44. Again, the components 34, 38, 40, 42 and 44 are illustrated merely to show how the spectral resolution of the reflected optical beams 36 could be enhanced.

With further reference to FIG. 1, the single optical beam 44 is directed into a first bandpass filter 54 that is intended to filter out all light except light of a certain wavelength. In this example, first bandpass filter 54 is a 640 nm bandpass filter, meaning that only light having a wavelength of 640 nm passes through the first bandpass filter 54. Light outside of this frequency is reflected by the first bandpass filter 54 towards a second bandpass filter 56. The second bandpass filter 56 is selected to have a bandpass wavelength of 660 nm, meaning that only light at 660 nm wavelength will pass through it. Arrows 58 represent a first reflected optical beam that has been filtered to include only light having a wavelength of 640 nm. Arrows 60 represent a second reflected optical beam that has been filtered to include only light having a wavelength of 660 nm.

The optical beam 58 subsequently passes through a lens 62 and impinges a first photodetector 64. Similarly, optical beam 60 passes through a focusing lens 66 before impinging a second photodetector 68. Each of the photodetectors 64 and 68 generate electrical output signals that are fed into processing subsystem 70. The electrical output signal from each photodetector 64 and 68 may be represented by the terms $V_{640}$ and $V_{660}$, respectively. The term $V_{640}$ represents the intensity (i.e., magnitude) of the optical beam either incident on detector 64, while $V_{660}$ represents the intensity (i.e., magnitude) of the optical beam 60 incident on detector 68.

When the cloud or plume 14 (representing the potential threat agent) is present around the sensor particles 12, this causes a shift in the spectral peak of light reflected from the particles 12. This shift in the spectral peak manifests itself by a reduction in the intensity of the first reflected optical beam 58 that is sensed by the detector 64. The first detector output voltage $V_{640}$ will then be less than the output voltage that would be expected if the sensor particles were present in air or in the presence of random dust particles. Conversely, the shifting of the spectral peak of the reflected light from the particles 12 causes an increase in the intensity of the second reflected optical beam 60. This increase in intensity is sensed by the second detector 68 and indicated by an increase in its output, $V_{660}$, beyond the predetermined value that would otherwise be produced if the sensor particles 12 were simply in the presence of air or random dust particles.

Figure 2:
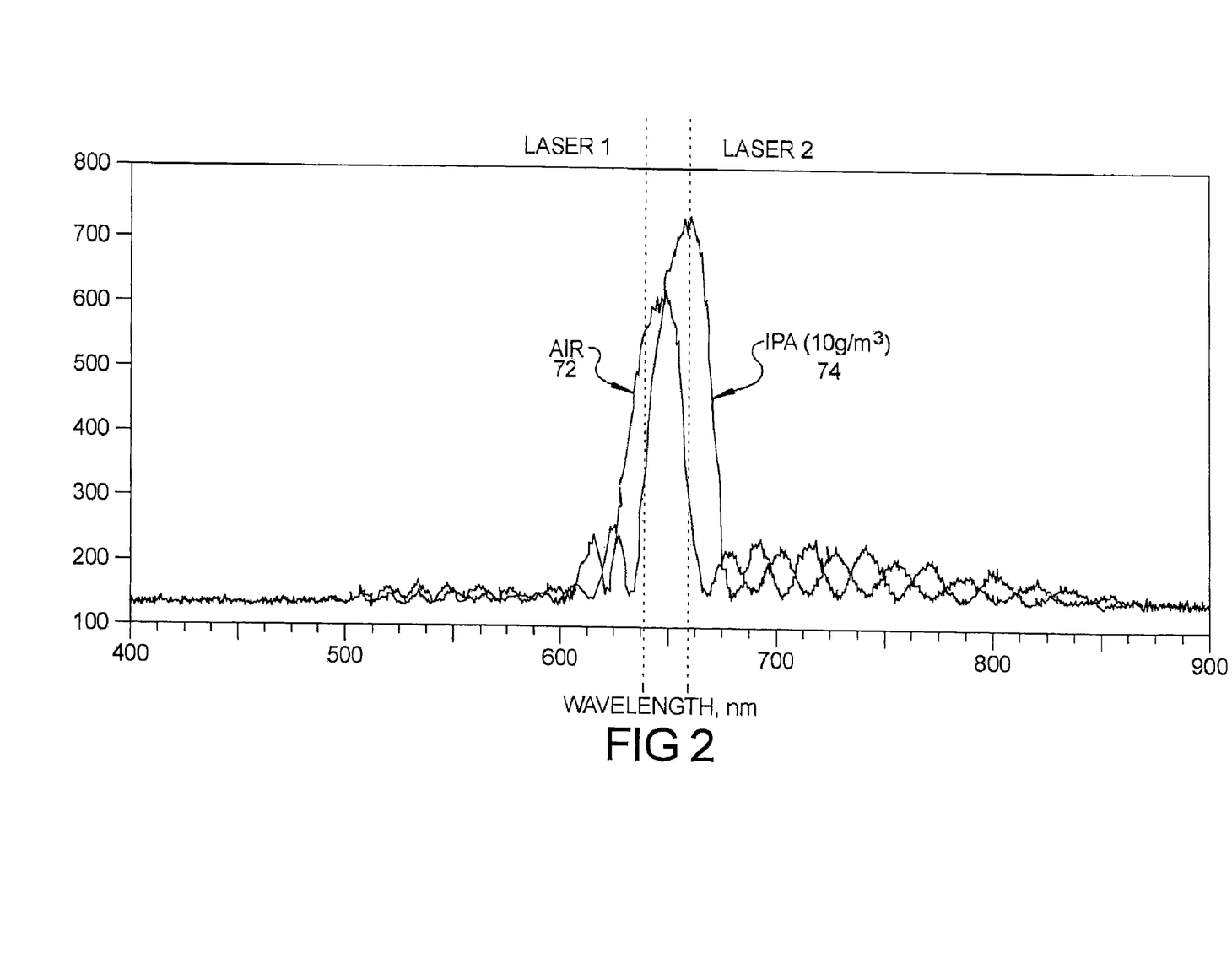
FIG. 2 is a graph illustrating the representative reflectivity spectra of the sensor crystals in air, and the shift in wavelength of light reflected from the crystals when the crystals are in the presence of isopropyl alcohol.
Figure 3:
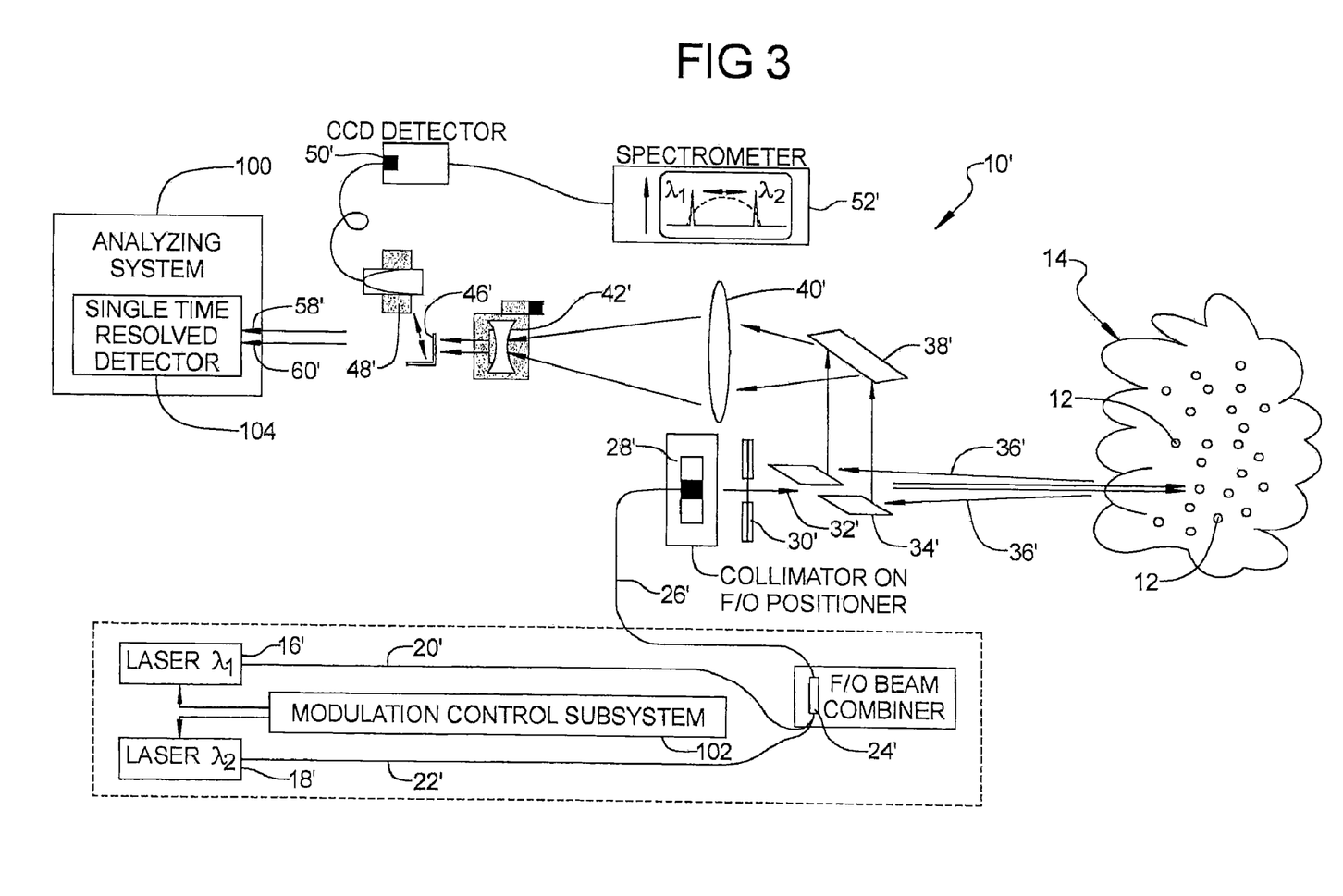
FIG. 3 is block diagram of an alternative embodiment of the system shown in FIG. 1 that makes use of a single time-resolved detector system for analyzing the reflected optical signals.
Figure 4:
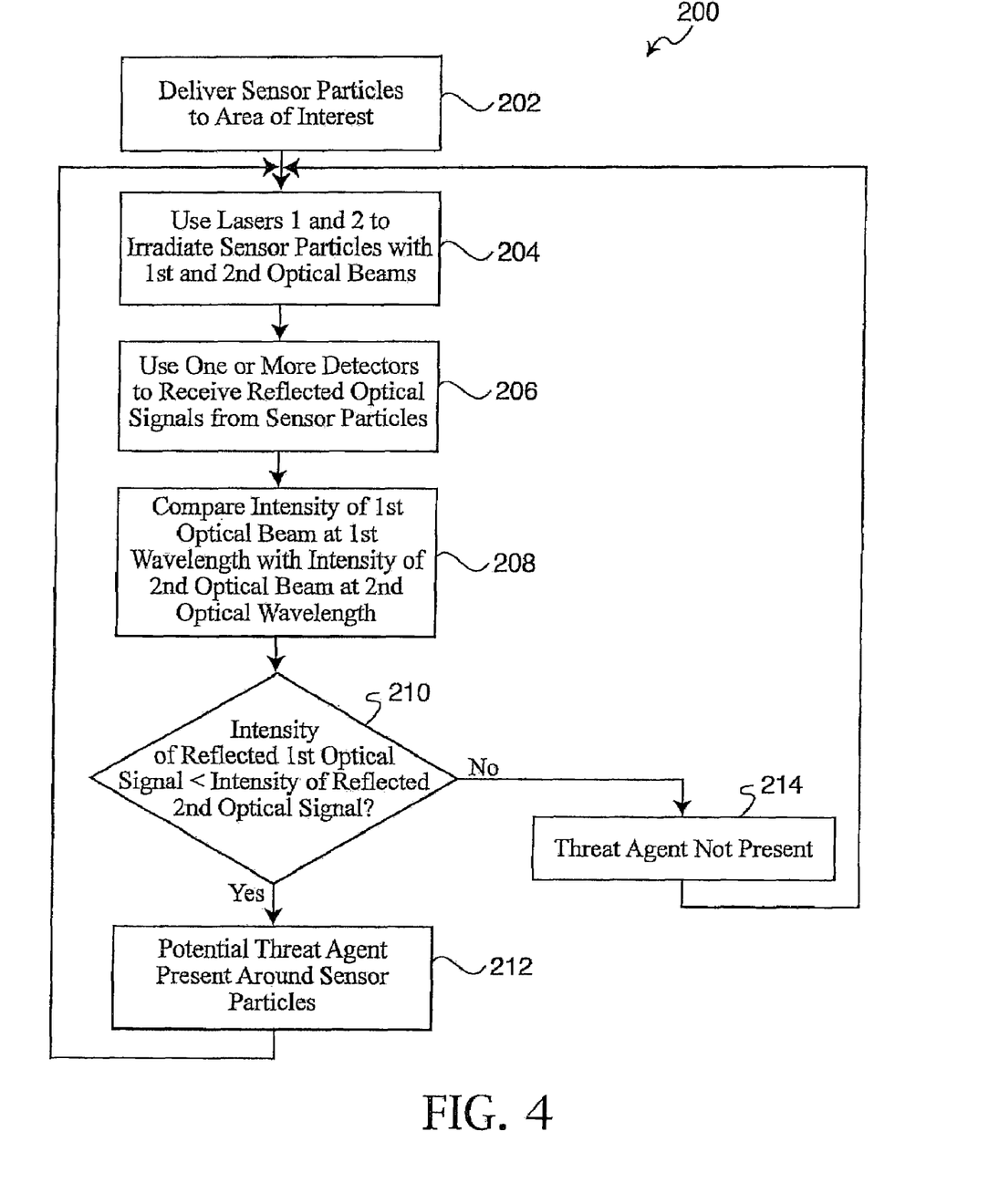
FIG. 4 is a flowchart of various operations that may be performed by the system of FIG. 1 in sensing the presence of a potential threat agent.

The spectral shifting of the light reflected from the sensor particles 12 is further illustrated in FIG. 2. FIG. 2 shows an exemplary waveform 72 that represents the light reflected by the sensor particles 12 when the sensor particles are simply dispersed in air or within random dust particles. It will be noted that waveform 72 has a spectral peak with a wavelength of about 640 nm. Waveform 74, however, illustrates the reflected light from the sensor particles 12 when the sensor particles are present within a cloud or plume of isopropyl alcohol (IPA). The spectral peak of waveform 74 has shifted to about 660 nm.

Returning to FIG. 1, it will be appreciated that during calibration of the system 10, the outputs of lasers 16 and 18 may be adjusted in intensity by reflecting their optical beams from isotropic, non-wavelength specific particles, for example, sand ($SiO_2$). The outputs from lasers 16 and 18 may then be adjusted so that the optical signals detected by the photodetectors 64 and 68 produce output signals having the same magnitude (i.e., so that $V_{660}$ is equal to $V_{640}$).

Referring further to FIG. 1, the processing subsystem 70 may be used to perform a summing operation to examine the output signals $V_{640}$ and $V_{660}$ from the photodetectors 64 and 68, to determine if a potential threat agent is present in the cloud or plume 14. When no potential threat agent is present, the output ($V_{660}$) from the second photodetector 68 will be less than the output ($V_{640}$) from the first photodetector 64. Thus, in the absence of a specific potential threat agent or random dust particles, the intensity of the reflected optical beam 58 at the 640 nm wavelength will be larger in intensity than the reflected optical beam 60 at the 660 nm wavelength. Thus, the quantity of $V_{660}$ minus $V_{640}$ will be a negative value, and the negative value indicates to a user of the system 10 that the sensor particles are present in free air.

When a specific potential threat agent is present, however, the light reflected from the sensor particles 12 experiences a shift in its spectral peak. This cause the intensity ($V_{660}$) of the second reflected optical beam 60 to be greater in magnitude than the intensity of the first reflected optical beam 58 ($V_{640}$). Thus, the quantity $V_{660}$ minus $V_{640}$ will be a positive value, and such a positive value signifies to the user that the sensor particles 12 and present within an area where the specific potential threat agent is present. When only air or random dust particles are present in the vicinity of the sensor particles 20, the $V_{660}$ minus $V_{640}$ quantity will be approximately zero. Thus, the processing subsystem 70 is able to discriminate whether the sensor particles 12 are present in a non-threatening atmosphere comprised of random dust particles, present within air, or present within a specific potential threat agent.

In view of the foregoing, it will also be appreciated while only two lasers 16 and 18 have been illustrated, that a greater or lesser plurality of lasers could be employed as well. The use of two lasers 16 and 18 and corresponding photodetectors 64 and 68 forms a "two channel" system that provides a degree of discrimination capability to detect whether a particular threat agent is present, but also to detect whether the sensor particles 12 are located within air or within another non-threatening particulate environment. Using a single laser 16 with a single detector, and with the processing subsystem 70 simply comparing the output of the detector to a predetermined threshold would still enable a "Yes"/"No" determination to be made as to whether or not a particular threat agent is present or not.

It will also be appreciated that the use of three or more lasers generating optical beams tuned to three or more wavelengths could also be employed to provide an even greater degree of discrimination/detection between different types of threat agents. Such a multi-channel system could be used to remotely detect for the presence of a plurality of distinct threat agents from a single remote site/location.

Referring to FIG. 3, an alternative embodiment of the system 10' is illustrated that makes use of a single, time-resolved detector system 100 and a modulation control subsystem 102. The other components of the system 10' shown in FIG. 3 are otherwise identical in construction and operation to those shown in FIG. 1, and thus a prime (') symbol has been used to denote common components with the embodiment of FIG. 1. The modulation control subsystem 102 modulates the two lasers 16' and 18' at two different temporal frequencies. The detector system 100 includes a single time-resolved detector 104 that may be synchronized to the two laser output signals, for example, alternately every 10 milliseconds, to alternately sample a first reflected optical beam 58' and a second reflected beam 60'. The intensities of the sampled, reflected optical beams 58 and 60 may then be compared to determine if the potential threat agent is present in the vicinity of the sensor particles 12.

Referring now to FIG. 4, a flowchart 200 is illustrated that presents a plurality of exemplary operations that may be performed by the system 10 during operation. In operation 202, the sensor particles 12 are delivered to an area of interest. In operation 204, the first and second lasers 16 and 18, respectively are used to irradiate the sensor particles 12 with the first and second optical beams. One or more detectors (64, 68 or 104) may then be used to receive the reflected optical signals 58 and 60 that are reflected from the sensor particles 12, as indicated in operation 206. In operation 208, the processing subsystem 70 is used to examine the outputs of the one more detectors (64, 68 or 104) and to examine the spectral peaks of the reflected optical beams 58 and 60. The peak comparison performed at operation 210 indicates that if the intensity of the first reflected optical beam is less than the intensity of the second reflected optical signal, then a determination is made that the potential threat agent is present in the vicinity of the sensor particles 12, as indicated at operation 212. Operations 204-210 may then be repeated as needed, for example, every 10-20 milliseconds. If the intensity of the reflected first optical beam 58 is greater than the intensity of the reflected second optical beam, then it is determined that the threat agent is not present, as indicated at operation 214. Operations 204-210 may then be repeated as needed.

The system 10 thus allows for the detection of one or more specific chemical, biological or other environmental agents that may pose a threat to individuals or to property. The system 10 is not limited to potential threat agents that are suspended in air, but could also just as readily be applied to the detection of volatile organic compounds in a liquid. The sensor particles 12 can be implemented as "microscopic tags" and used in tracking substances, and substances in liquid form. Other specific applications of the system and method of the present disclosure could be in various military and industrial applications to remotely test for the presence of specific, harmful chemical or biological agents. Still further applications could be in connection with the sensing of deleterious volatile organic compounds in the presence of foods and/or drugs.

While the system 10 is especially well suited for the detection of condensable, organic vapors, other methods to induce the shift in the photonic resonance of the porous photonic crystals that are used to form the sensor particles may also be used. For example, a shift in the photonic resonance of the porous photonic crystals could be achieved by placing the sensor particles 12 in the presence of various other chemical and biological compounds, that results in chemical reactions caused by the presence of corrosive species, for example, chlorine, ammonia, or ozone, and catalyzed reactions of chemical agents (e.g., the catalytic hydrolysis of the nerve agent Sarin to produce HF).

The system and method 10 thus enables the detection of volatile compounds in air or in water from remote distances using low power lasers. The system and method 10 provides the advantage that chemical "specificity" can be incorporated into the sensor particle design so that the system is designed to detect specific chemical or biological agents.

While various embodiments have been described, those skilled in the art will recognize modifications or variations which might be made without departing from the present disclosure. The examples illustrate the various embodiments and are not intended to limit the present disclosure. Therefore, the description and claims should be interpreted liberally with only such limitation as is necessary in view of the pertinent prior art.

What is claimed is:

1. A system for free space, optical remote sensing for a potential threat agent, the system comprising:
   a laser system for emitting two beams of coherent light at first and second different wavelengths;
   a sensor agent located remotely from said laser system that is irradiated by said laser system, the sensor agent having a characteristic such that a wavelength of a reflected spectral peak thereof closely approximately matches said first wavelength, in the absence of said potential threat agent, and such that said reflected spectral peak changes in wavelength from said first wavelength when said sensor agent is exposed to potential threat agent; and
   a detector system that receives and analyzes said beams of coherent light generated by said laser system that is reflected from said sensor agent, to determine if a shift in said reflected spectral peak away from said first wavelength has occurred, indicating a presence of said potential threat agent.

2. The system of claim 1, wherein said laser system comprises first and second lasers, with said first laser being tuned to emit a first one of said beams of coherent light at said first wavelength, and said second laser tuned to emit a second one of said beams of coherent light at said second wavelength.

3. The system of claim 2, wherein said first and second lasers are modulated at different temporal frequencies.

4. The system of claim 1, wherein said detector system determines if said reflected spectral peak has shifted away from said first wavelength toward said second wavelength.

5. The system of claim 4, wherein said detector system includes:
   a first detector for detecting an amplitude of a first reflected spectral peak at said first wavelength;
   a second detector for detecting an amplitude of a second reflected spectral peak at said second wavelength; and
   a system for processing said detected amplitudes to determine if said amplitude of said first reflected spectral peak has been reduced in magnitude while said amplitude of said second reflected spectral speak has increased in spectral magnitude, thus indicating the presence of said potential threat agent.

6. The system of claim 5, wherein:
   said first detector includes a first bandpass filter that passes only optical radiation having said first wavelength; and
   said second detector includes a second bandpass filter that passes only optical radiation having said second wavelength.

7. The system of claim 1, wherein said sensor agent comprises porous photonic crystals.

8. The system of claim 1, wherein said system for processing said detected amplitudes comprises a single time-resolved detector.

9. A method for free space, optical remote sensing for a potential threat agent, the method comprising:
   a) forming a sensor having a characteristic such that optical radiation impinging the sensor and reflected from the sensor has a spectral peak with a first wavelength;
   b) directing a first optical beam of coherent light having said first wavelength at said sensor;
   c) directing a second optical beam of coherent light having a second wavelength that is different than said first wavelength at said sensor;
   d) analyzing said first and second optical beams of coherent light after said beams have been reflected from said sensor to determine if one of said optical beams has experienced a spectral shift; and
   e) interpreting said spectral shift as indicating the presence of said potential threat agent.

10. The method of claim 9, wherein operations a) and b) comprise using a pair of lasers modulated at first and second temporal frequencies, to generate said first and second optical beams, respectively.

11. The method of claim 9, wherein operations a) and b) comprise using first and second lasers that simultaneously generate said first and second optical beams.

12. The method of claim 9, wherein operations a) and b) comprise using a single laser with a tunable emission energy, where the laser emission wavelength is scanned and detected over a range of energies that encompass the energies of the first and second peaks of the sensor.

13. The method of claim 9, wherein operation d) comprises using a single time-resolved detector to receive said first and second optical beams after said beams have been reflected from said sensor.

14. The method of claim 9, wherein operation d) comprises using separate detectors to measure an amplitude of each of said optical signals.

15. The method of claim 14, wherein operation a) comprises forming said sensor material from porous silicon photonic crystals.

16. The method of claim 9, wherein operation a) comprises forming a sensor from porous silicon photonic crystals.

17. A method for free space, optical remote sensing for a potential threat agent, the method comprising:
   a) forming a sensor from spectrally responsive sensor material having a characteristic such that optical radiation impinging the sensor material and reflected from the sensor material has a spectral peak at a predetermined wavelength, when said potential threat agent is not present in a vicinity of said sensor material;

b) using first and second optical beams of coherent light having different wavelengths to irradiate said sensor material, at least one of said wavelengths being approximately equal to the predetermined wavelength; and c) analyzing said first and second optical beams of coherent light after said beams have been reflected from said sensor material to determine if said spectral peak of one of said reflected optical beams has shifted, said shifting indicating the presence of said potential threat agent.

18. The method of claim 17, wherein operation a) comprises forming said sensor material from porous photonic crystals.

19. The method of claim 17, wherein operation c) comprises receiving said first and second optical beams reflected from said sensor material with separate detectors.

20. The method of claim 19, wherein operation c) further comprises using a pair of filters to provide said reflected optical beams to said detectors.

* * * * *